United States Patent [19]

Vegezzi

[11] 4,140,777

[45] Feb. 20, 1979

[54] CEREBRAL VASODILATING 6-SUBSTITUTED VINCAMINES

[75] Inventor: Davide Vegezzi, Massagno, Lugano, Switzerland

[73] Assignee: Enrico Corvi Mora, Piacenza, Italy

[21] Appl. No.: 801,793

[22] Filed: May 31, 1977

[30] Foreign Application Priority Data

Jun. 3, 1976 [CH] Switzerland ............................ 704176

[51] Int. Cl.$^2$ .................. C07D 519/04; A61K 31/445
[52] U.S. Cl. ....................................... 424/256; 546/51
[58] Field of Search ...................... 260/293.53, 293.55; 424/256, 267

[56] References Cited

FOREIGN PATENT DOCUMENTS 2175317 10/1973 France ........................................ 546/51

OTHER PUBLICATIONS

Wiberg, K. B. et al., (Ed), *Oxidation in Organic Chemistry*, part A, Academic Press, New York, 1965, pp. 105–106.

House, H. O.,*Modern Synthetic Reactions*, 2nd Ed., W. A. Benjamin, Inc., Menlo Park, Cal., 1972, pp. 49–51 (I) and 345–355 (II); 1st Ed., 1965, p. 31 (III).

Foerst, W., *Newer Methods of Preparative Organic Chemistry*, vol. IV, Academic Press, New York, 1968, pp. 224–227.

Fieser, L. F. et al., *Reagents for Organic Synthesis*, vol. 1, John Wiley and Sons, Inc., New York, 1965, p. 620.

House, H., *Modern Synthetic Reactions*, W. A. Benjamin, New York, 1965, p. 84.

*Primary Examiner*—Henry R. Jiles
*Assistant Examiner*—Richard A. Schwartz
*Attorney, Agent, or Firm*—Stevens, Davis, Miller & Mosher

[57] ABSTRACT

The invention relates to novel derivatives of vincamine and apovincamine having the formula which are endowed with analogous properties as the vincamine and apovincamine as well as with an extended effect. The invention relates also to the methods for the preparation of the above derivatives.

8 Claims, No Drawings

1

CEREBRAL VASODILATING 6-SUBSTITUTED VINCAMINES

The present invention relates to novel derivatives of the vincamine having the formula

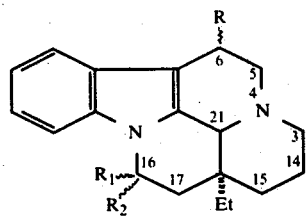

wherein R represents —OH, =O; $R_1$ is OH or is absent and $R_2$ is $COOCH_3$, $CH_2OH$, a double bond $\Delta^{16,17}$ being present when $R_1$ is absent or when $R_1 + R_2$ is =O. The present invention also concerns the methods for the preparation of the above compounds.

More particularly, the compounds of the present invention corresponding to the preceding general formula comprise 6-hydroxyvincamine, 6-ketovincamine, 6-ketovincaminol, 6-ketoapovincamine, 6-keto-16-epivincamine and 6-ketovincamone(6-oxovincamone).

As regards the method according to the present invention it is to be firstly pointed out that, to date, the action of the oxidizing agents on the vincamine gave place to products of the type $\Delta^{4,21}$-vincamine or N-oxides thereof.

It has been now surprisingly found that the compounds of the present invention can be prepared starting from vincamine, epivincamine or apovincamine, depending on the desired final product, through a method of oxidation essentially characterized in that compounds of hexavalent chromium are used as the oxidizing agents. The methods according to the present invention shall be better understood from the following scheme:

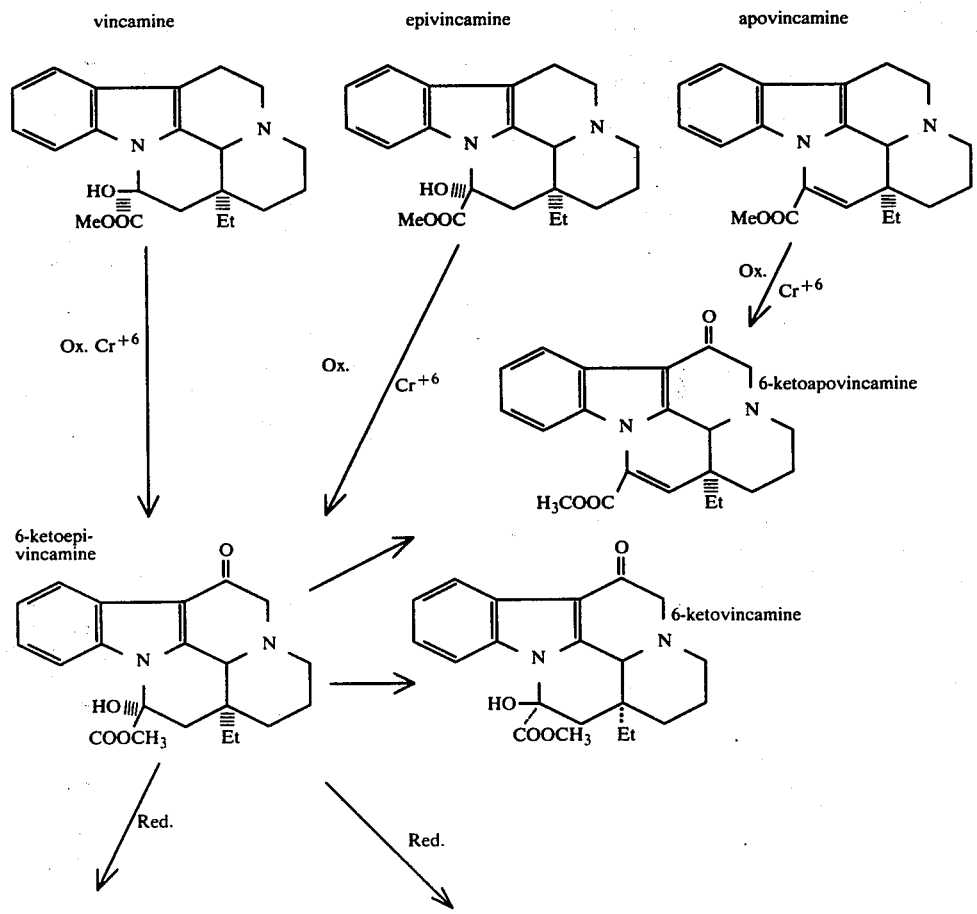

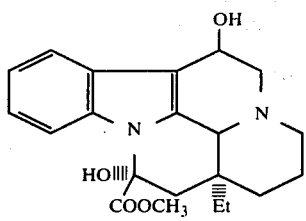
6-hydroxyepivincamine

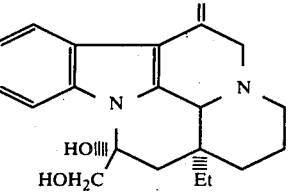
6-ketovincaminol

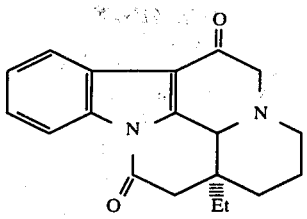
6-ketovincamone

From the preceding scheme it clearly appears that through the method of the present invention the use of compounds of hexavalent chromium as the oxidizing agents leads selectively to the oxidation in the $C_6$ position, the 6-ketoderivatives being thus formed, the structures of which are undoubtedly confirmed by the mass spectrometry examination.

It is surprising that 6-ketovincamine is obtained from the epivincamine, since in the reaction with chromic acid there is simultaneously carried out the oxidation of the $C_6$ carbon atom and the stereochemical inversion at the $C_{16}$ position. Thus the 6-keto-16-vincamine is not only prepared from the 16-epivincamine, but it can be also prepared through an epimerization of the 6-ketovincamine by reacting the latter with a strong base.

The 6-hydroxyvincamine and the 6-ketovincaminol are prepared by chemical reduction of the 6-ketovincamine under particular conditions, whereas the 6-ketovincamone is suitably prepared by oxidation of 6-ketovincaminol.

The features and advantages of the present invention both as regards the compounds and as regards the related preparation, shall appear from the following examples, having illustrative but not limitative purpose.

EXAMPLE 1

6-ketovincamine

In a suitable flask, provided with cooling means, thermometer, stirrer and dropwise charging funnel, a solution of 20 g of vincamine as the free base in a mixture of 50 mls of 50% sulfuric acid and 1000 mls of dry acetone, distilled over $CrO_3$, is prepared.

Under stirring and at room temperature, the content of the flask is dropwise supplemented with 35 mls of an acetone solution of chromic acid (8N–Jones reactant). At the end of the addition, the mixture is maintained on standing for a night. The conversion is monitored by means of this layer chromatography (TLC), by using silica gel ($GF_{254}$ sodium Merck (2.5%)) as the adsorbant and a mixture of $CHCl_3$ and MeOH (96:4) as the eluant.

The chromatogram is revealed under U.V. light at $\lambda = 254$ nm.

Upon the disappearance of the spot of the vincamine, the excess of the oxidizing agent is decomposed with isopropanol, whereafter the reaction mixture is filtered, diluted with water (volume/ volume), made alkaline at room temperature with concentrated $NH_4OH$ to pH 9 and repeatedly extracted with $CHCl_3$ until the liquor is exhausted.

The combined organic extracts are washed with water, dried over $Na_2SO_4$, filtered and the $CHCl_3$ is evaporated under reduced pressure until a dry residue is obtained. There are obtained 9 g of a solid raw product, which can be recrystallized from ethanol and acetone.

The 6-ketovincamine is a white, crystalline solid having the following properties:

melting point: 240–241° C.

analysis: for $C_{21}H_{24}N_2O_4$ M = 368.41. Calculated: C = 68.46%; H = 6.566%; N = 7.60%. Found: C = 68.31%; H = 6.6%; N = 7.52. U. V. spectrum in MeOH: $\lambda_{1max} = 241$ nm, $\lambda_{2max} = 265$ nm, $\lambda_{3max} = 295$ nm I. R. spectrum (Nujol), bands at:

| | |
|---|---|
| 3400 cm$^{-1}$ | $\gamma$—OH    enlarged |
| 1740 cm$^{-1}$ | $\gamma$C = O of —COOCH$_3$ (ester) |
| 1640 cm$^{-1}$ | $\gamma$C = O of $\diagdown$C = O conjugated $\diagup$ |

Mass spectrum: molecular ion M$^+$ = 368 m/e other peaks at m/e 339 (M-$C_2H_5$), 309 (M-COOCH$_3$), 298 (M-70).

The preparation of the 6-ketovincamine can be also carried out starting from 16-epivincamine.

The above experimental conditions are repeated, the 16-epivincamine undergoing both the oxidation at the $C_6$ methylene, and the stereochemical inversion at the $C_{16}$ substituents.

EXAMPLE 2

6-ketoapovincamine

According to the method of the Example 1, the oxidation is effected on 10 g of apovincamine.

At the end of the reaction, 4 g of raw product are obtained, which are chromatographed on a silica gel column, a mixture of $CHCl_3$ and MeOH (98:2) being used as the eluant.

By concentrating the initial fractions, 1.2 g of 6-ketoapovincamine are obtained, in form of an amorphous substance, having mass 350 m/e.

EXAMPLE 3

6-ketovincaminol 1.5 g of 6-ketovincamine are dissolved into 300 mls of tetrahydrofuran (THF) containing 5% water. The solution is supplemented with 250 mg of $NaBH_4$ and maintained at room temperature under stirring for 30 minutes. At the end of this time further 250 mg of $NaBH_4$ are added and, after 30 minutes, the disappearance of the 6-ketovincamine is monitored by TLC (silica gel, benzene/acetone/ethanol = 75:15:10, iodine vapours). At the end of the reduction, the reaction mixture is treated with 800 mls of water and with an amount of diluted hydrogen chloride enough to bring the pH to about 1. A first extraction is carried out with 3 × 300 mls of diethyl ether; then the aqueous phase is made alkaline with 10% $NH_4OH$ and extracted with 3 × 300 mls of CHCl₃, the final exhaustion being effected with 3 × 200 mls of EtOH/CHCl₃ (2:3) mixture.

The extracts of the alkaline phases are combined, dried over Na₂SO₄, filtered and concentrated to a residue.

About 1 g of product is obtained, which is purified by means of two column chromatographies.

From the first chromatography (silica gel, benzene/acetone/EtOH = 75/15/10), there are obtained 750 mg of a mixture enriched with the component having Rf = 0.26, and 150 mg of a pure product, which is identified as 6-hydroxyvincamine, whereas from the second chromatography (as effected in an apparatus for liquid, low pressure, chromatography, of the Merck type, standard columns, CHCl₃/AcOEt/EtOH = 20/20/5 eluant), after concentration of the useful fractions, there are obtained 500 mg of a TLC pure product.

The 6-ketovincaminol, as recrystallized from ethanol, has the following chemical and physical properties:

Melting point = 220° C. with decomposition

IR spectrum (KBr) bands at: 3300 cm$^{-1}$ enlarged $\nu$O—H. 1625 cm$^{-1}$ $\nu$C=O conjugated.

U.V. spectrum (MeOH) $\lambda_{1max}$ = 243 nm, $\lambda_{2max}$ = 266 nm, $\lambda_{3max}$ = 302 nm.

Analysis: for $C_{20}H_{24}N_2O_3$ (M = 340). Calculated: C = 70.56%; H = 7.11%; N = 8.23%. Found: C = 70.31%, H = 7.05%; N = 8.28%.

Mass spectrum: molecular ion at 340 m/e.

EXAMPLE 4

6-hydroxyvincamine

A solution of 3.68 g of 6-ketovincamine, as prepared according to the Example 1, in 1000 mls of methanol is supplemented under stirring with 1 g of NaBH₄, in form of several 200 mg fractions over about 30 minutes.

At the end of the addition, the mixture is maintained for about 1 hour at room temperature and then treated with diluted hydrogen chloride until the pH is 6-7. The solution is subsequently brought to alkaline pH by adding, still at room temperature, 20% NH₄OH, diluted with water and extracted with CHCl₃.

The combined organic extracts are washed with water to neutrality, dried over Na₂SO₄, filtered and concentrated to a small volume.

The residue solution is treated by column chromatography, silica gel being used as the adsorbant and a mixture of benzene/acetone/ethanol in the ratio 75/15/10 (eluant A) being used as the eluant. There are collected the useful fractions, comprising the products having Rf of between 0.15 and 0.30 (TLC: silica gel G, eluant A, revealing with cerium ammonium sulfate under U.V. light at 366 nm), and these fractions, after being suitably combined and concentrated, are subjected to a second purification by column chromatography, a mixture of CHCl₃/acetone/MeOH = 70/20/8 (eluant B) being used as the eluant.

The 6-hydroxyvincamine is obtained by concentrating the fractions having Rf = 0.20 (eluant A) and is in form of an amorphous product having the following spectroscopic properties:

I.R. spectrum (CHCl₃ bands at: 3400-3500 cm$^{-1}$ enlarged $\nu$OH. 1730 cm$^{-1}$ $\nu$C=O of —COOCH₃.

U.V. spectrum (MeOH): $\lambda_{1max}$ = 222 nm $\lambda_{2max}$ = 276 nm

Mass spectrum: molecular ion M$^+$ = 370 m/e other peaks at m/e 351 (M—H₂O—H); m/e 352 (M—H₂O) m/e 323 (M—C₂H₅—H₂O); m/e 300 (M—70); m/e 282 (M—70—H₂O).

EXAMPLE 5

6-keto-16-epivincamine 3 g of 6ketovincamine are dissolved into 370 mls of absolute tetrahydrofuran and the solution is supplemented with 4.15 g of LiAlH(t-BuO)₃, the temperature being maintained at 20° C. The mixture is maintained under stirring for 3 hours and then is cautiously treated with 20 mls of water, the resulting reaction mixture being thereafter poured into 1000 mls of water. The mixture is then filtered on Celite and thoroughly washed on the filter with CHCl₃.

The filtrate is made alkaline, extracted until exhausted with CHCl₃, and the combined organic extracts are dried over Na₂SO₄, filtered and concentrated to a dry residue under reduced pressure.

There are obtained 2 g of a residue which is taken with 100 mls of hot acetone, and thereafter the mixture is heated to boiling and the volume is brought to 50 mls.

After cooling, there are obtained 1.2 g of a crystalline, solid substance, having chemical and physical properties corresponding to those of the starting 6-ketovincamine.

The acetone filtrate, upon concentration to a dry residue, gives place to 800 mg of a mixture comprising 6-ketovincamine and a product having lower Rf (eluant: CHCl₃/MeOH = 96:4; absorbant: GF₂₅₄ silica gel). The acetone residue is treated by chromatography on a silica gel column and eluted with a mixture of CHCl₃/MeOH in the ratio 9:1.

From the initial fractions there are recovered 250 mg of 6-ketovincamine, whereas from the subsequent fractions, after solvent evaporation, 200 mg of the 6-keto-16-epivincamine isomer are obtained.

The isomer is distinguished from the 6-keto-vincamine only by the Rf value, the IR spectra and the mass fragmentation spectra being identical.

EXAMPLE 6

6-ketovincamone 3 g of 6-ketovincaminol are dissolved into 60 mls of tetrahydrofuran under nitrogen atmosphere. The resultant solution is dropwise supplemented with a mixture comprising 2.1 g of H₅IO₆ in 120 mls of THF, the reaction mixture being maintained at room temperature and under stirring for 3 hours.

The reaction is completed by adding further 500 mg of H₅IO₆, whereafter the reaction mixture is maintained on standing for a night.

The mixture is then poured into 250 mls of water, made alkaline with 10% NH₄OH up to pH 8 and extracted with CHCl₃.

The combined chloroformic solutions are dried over Na₂SO₄, filtered and concentrated to a dry residue under reduced pressure.

The residue is taken with acetone, dried again, and the product is recrystallized from ethanol.

There are obtained 2 g of a crystalline substance having the following chemical and physical properties:
melting point: 197°-199° C.

Analysis: for $C_{19}H_{20}N_2O_2$ calculated C = 73.9%; H = 6.54%; N = 9.08%. found C = 72.8%; H = 6.44%; N = 8.98%.

MS M$^+$ = 308 m/e

IR spectra bands at 1725 cm$^{-1}$ $\nu$CO. 1675 cm$^{-1}$ $\nu$CO conjugated.

The vincamine and the apovincamine are substances already known and used in the therapy of the cerebral arteriosclerosis, owing to their effective vasodilating action at the cerebral level and furthermore due to their capacity of activating the metabolism of the nervous cells.

However their therapeutical action, through the several administration routes, is characterized by a short duration, as a consequence of their ready elimination, whereby repeated administration, within the 24 hour period are necessary.

It has been found, which is another object of the present invention that the derivatives of the vincamine and of the apovincamine of the present invention are endowed with the property of possessing analogous therapeutical activity combined with an effect which is extended in the time, namely of the so-called longacting type.

The novel derivatives according to the present invention have been subjected to a pharmacological investigation, in which the following aspects were particularly examined, in order to point out not only the pharmacological activity at the cerebral level, but also under the pharmacokinetic point of view in order to demonstrate a delayed absorption and distribution.

The following properties have been examined:
Acute toxicity per intraperitoneal route
Hematic levels at different times from the oral administration
Variation of the hematic flow at different times from the intravenous administration
Blood platelet respiration.

A — Acute toxicity

The acute toxicity was assessed in the mouse of the Swiss type, having an average body weight of 20 g and of male sex, groups of 5 animals being used, according to the method of Litchfield and Wilcoxon (observation time: 8 days). The compounds were administered as a suspension in 1% carboxymethylcellulose.

The acute toxicity was low for all the examined compounds, as confirmed by the following table, in which those of the vincamine HCl and of the apovincamine are also reported.

The results confirm therefore that the compounds, when administered by the parenteral route, are scarcely toxic. In fact, for all the compounds, the toxicity, when evaluated according to the method of Gleason, can be classified as light, modest or negligible.

B — Absorption

All the compounds have been orally administered at the dosage of 100 mg/kg, expressed as vincamine and apovincamine, in form of a suspension in a 5% carboxymethyl cellulose solution.

The absorption was determined by evaluating the hematic levels at the following times (minutes): 0, 30, 120, 240, 480, 10 hours and 12 hours, at which it was possible to assess the time, from the administration, of the maximum hematic concentration.

The vincamine and apovincamine concentrations were assessed by chromatographic method.

For the evaluation of the prolonged action the following criterium was adopted; as derivatives having a long-acting effect, there are considered those which, 120 minutes after the administration, show hematic levels higher than those obtained with vincamine and apovincamine.

From the TABLE it is evident that the compounds of the invention give place to the maximum hematic levels at times definitely higher than those of the vincamine HCl, whereby an effect of the long-acting or prolonged type is confirmed.

C — Hematic flow

The cerebral vasodilating activity was studied in the anestetized dog, by measuring, by means of Statham periarterial electromagnetic flowmeters, the hematic flow at the level of the vertebral arteria which, in such animal species, constitutes the greatest blood supply to the brain.

The compounds, when injected through the femoral vein at doses corresponding to 5 mg/kg, caused increases of the hematic flow directed to the brain at least comparable and some times even higher than those of the vincamine.

The results are reported in the TABLE as the percent variations of the flow measured at the level of the left vertebral arteria after the administration of the several compounds to be tested to groups of 4 animals for each compound. The results also confirm that the compounds of the invention are all endowed with a vasodilating activity at the level of the cerebral circulus. Such an action for some compounds is more relevant with respect to that of vincamine and of apovincamine.

D — Blood platelet respiration

From the tests carried out in vivo in the rabbit it resulted that the compounds of the present invention are capable of enhancing the respiratory parameters of the blood platelets.

On the basis of the above considerations both of oxicological and of pharmacokinetic and pharmacodynamic nature it can be thus stated that the compounds of the present invention can be used both per oral route and by parenteral route in order to obtain a pharmacological effect of the long-acting type.

It is worth to point out that, through the administration of these compounds, it is possible to reduce the dosage of vincamine the therapeutical action being maintained or even improved.

Suggested daily dosage: 40–160 mg.

TABLE

|  | Ex. No. | LD$_{50}$ in the mouse mg/kg i.p. | Tox (Gleason) | max.conc. time (minut.) | % Variations (*) |
|---|---|---|---|---|---|
| Vincamine HCl | — | 800 | modest | 20 | +24.1 |
| Apovincamine | — | >2000 | negligible | 60 | +25.6 |
| 6-ketovincamine | 1 | >2000 | " | 60 | +28.4 |
| 6-ketoapovincamine | 2 | >2000 | " | 60 | +29.2 |
| 6-ketovincaminol | 3 | 1500 | light | 120 | +30.2 |
| 6-hydroxyvincamine | 4 | 900 | modest | 60 | +33.4 |
| 6-keto-16-epivincamine | 5 | >2000 | negligible | 240 | +35.7 |
| 6-ketovincamone | 6 | >2000 | " | 240 | +30.2 |

(*) Percent variations of the hematic flow at the vertebral arteria after i.v. administration in the dog.

I claim:
1. A vincamine compound having the formula:

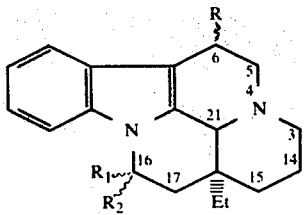

wherein R is —OH, =O,
R₁ is OH or is absent and
R₂ is COOCH₃, CH₂OH, a double bond in the $\Delta^{16,17}$ position being present when R₁ is absent or R₁ + R₂ R₂ = =O.

2. The compound according to claim 1, which is 6-ketovincamine.
3. The compound according to claim 1, which is 6-hydroxyvincamine.
4. The compound according to claim 1, which is 6-ketovincaminol.
5. The compound according to claim 1, which is 6-ketovincamone.
6. The compound according to claim 1, which is 6-keto-16-epivincamine.
7. The compound according to claim 1, which is 6-ketoapovincamine.
8. A cerebral vasodilating composition, comprising 40–160 milligrams daily dosage of a vincamine derivative according to claim 1 in a pharmaceutically acceptable excipient.

* * * * *